DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED DECEMBER 19, 1972

905 O.G. 452

T905,003

HYDROPEROXIDE CONVERSION AND EPOXIDATION CATALYST

William M. Bunting, 1311 N. Foster Drive 70806, and Clyde L. Aldridge, 6022 S. Pollard Parkway 70808, both of Baton Rouge, La.

Filed Sept. 30, 1971, Ser. No. 185,411

**Int. Cl. C07d *1/08***

U.S. Cl. 260—348.5 L

No Drawing. 16 Pages Specification

Olefin-containing streams are reacted with hydroperoxide-containing streams in a reaction zone operating at temperatures between minus 20° and 200° C. and at pressures sufficient to maintain a liquid phase, and additionally in the presence of a supported, Group VB–VIIB metal catalyst, such as chromium oxide supported on silica to produce an epoxide-containing stream, which epoxides may be utilized in various chemical reactions or subsequently converted into alcohols for gasoline blending and hydroperoxide derivatives which have value such as in gasoline blending or which may be reconverted to hydroperoxides. Hydrogenation using the same catalyst may follow the epoxidation reaction.